United States Patent [19]
Virta

[11] Patent Number: 5,728,930
[45] Date of Patent: Mar. 17, 1998

[54] METHOD AND DEVICE FOR MEASURING THE PERMEABILITY OF A DRYING WIRE TO AIR

[75] Inventor: Raimo Virta, Turku, Finland

[73] Assignee: Valmet Corporation, Helsinki, Finland

[21] Appl. No.: 735,782

[22] Filed: Oct. 23, 1996

[30] Foreign Application Priority Data

Oct. 23, 1995 [FI] Finland .................. 955039
Jan. 17, 1996 [FI] Finland .................. 960220

[51] Int. Cl.$^6$ ................... G01N 815/08
[52] U.S. Cl. ............... 73/38; 73/189; 34/114
[58] Field of Search .............. 34/114, 115, 116, 34/117; 73/38, 159

[56] References Cited

U.S. PATENT DOCUMENTS

| | | | |
|---|---|---|---|
| 3,138,014 | 6/1964 | Jorre | 73/38 |
| 3,668,787 | 6/1972 | Nils-Christian | 34/111 |
| 4,471,649 | 9/1984 | Cronshaw | 73/36 |
| 4,602,439 | 7/1986 | Pekka | 34/456 |
| 4,625,430 | 12/1986 | Aula | 34/392 |
| 4,676,091 | 6/1987 | Schuster et al. | 73/38 |
| 4,692,215 | 9/1987 | Kerttula | 162/289 |
| 4,694,587 | 9/1987 | Eskelinen | 34/457 |
| 4,730,481 | 3/1988 | Schlipf | 73/38 |
| 4,889,598 | 12/1989 | Niskanen | 34/117 |
| 4,892,621 | 1/1990 | Eskelinen | 162/196 |
| 4,905,380 | 3/1990 | Eskelinen | 34/457 |
| 4,905,500 | 3/1990 | Mason | 73/38 |
| 4,932,138 | 6/1990 | Liedes | 34/456 |
| 4,953,297 | 9/1990 | Eskelinen | 34/457 |
| 4,991,425 | 2/1991 | Gulya et al. | 73/38 |
| 4,992,142 | 2/1991 | Nguyen | 162/198 |
| 4,996,782 | 3/1991 | Eivola | 34/114 |
| 5,019,213 | 5/1991 | RaimoVirta | 162/193 |
| 5,094,718 | 3/1992 | Friend | 162/98 |
| 5,115,581 | 5/1992 | Viitanen | 34/115 |
| 5,163,236 | 11/1992 | Heikkila | 34/115 |
| 5,383,287 | 1/1995 | Kuhasalo | 34/117 |
| 5,393,383 | 2/1995 | Karvinen | 162/274 |
| 5,426,867 | 6/1995 | Yli-Kauppila | 34/452 |
| 5,495,678 | 3/1996 | Ilmarinen | 34/117 |
| 5,534,116 | 7/1996 | Karvinen | 162/274 |
| 5,535,527 | 7/1996 | Virta | 34/117 |
| 5,555,638 | 9/1996 | Lehosvuo | 34/117 |

FOREIGN PATENT DOCUMENTS

| | | |
|---|---|---|
| 0107482 | 5/1984 | European Pat. Off. |
| 0240881 | 10/1987 | European Pat. Off. |
| 0307289 | 3/1989 | European Pat. Off. |
| 3830308 | 4/1989 | Germany. |
| 4217682 | 11/1993 | Germany. |
| 2093597 | 9/1982 | United Kingdom. |

Primary Examiner—Hezron E. Williams
Assistant Examiner—Jay L. Politzer
Attorney, Agent, or Firm—Steinberg, Raskin & Davidson, P.C.

[57] ABSTRACT

A method and device for measuring the permeability of a drying wire to air in which the measurement is carried out continuously while the drying wire moves. The drying wire is guided to run so that it passes over a blow box and a measurement box free of contact, and the pressure in the measurement box and/or the relative change in the pressure is/are measured when the blow box is creating a pressure differential between the blow box and the measurement box in the vicinity of the wire. The pressure and/or the relative change in the pressure is/are compared with earlier measurement results and/or starting values (reference values). The permeability to air of the drying wire is determined on the basis of comparison of the pressure and/or of the relative change in the pressure, and the contact-free measurement is produced by guiding the flow into or out of the measurement box to pass through a gap between the measurement box and the drying wire.

20 Claims, 3 Drawing Sheets

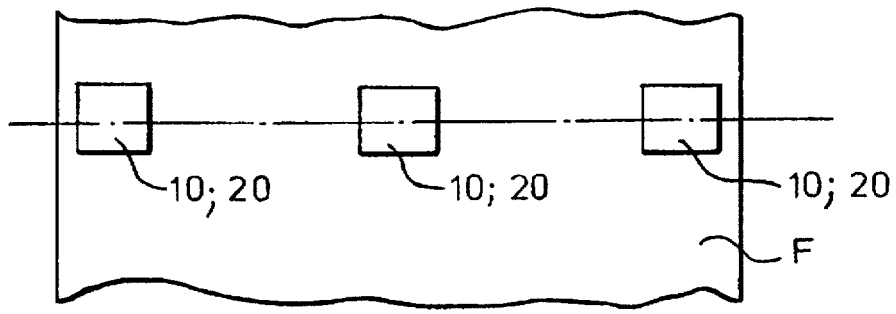
FIG. 6
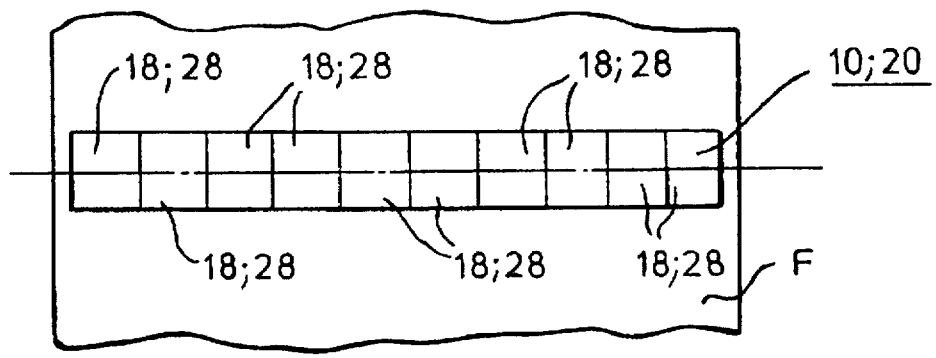
FIG. 7
FIG. 8
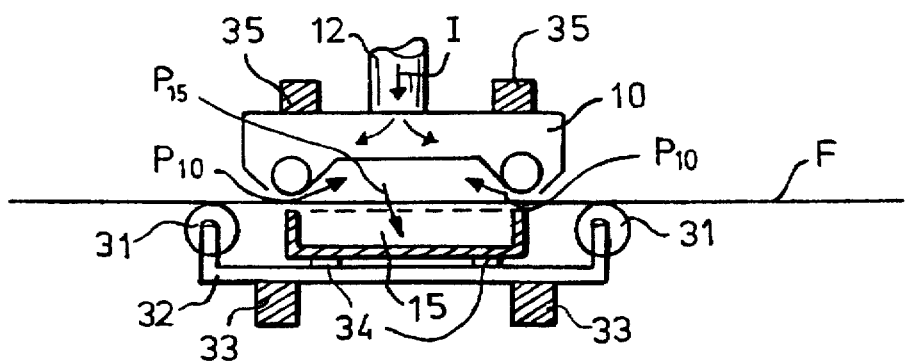

METHOD AND DEVICE FOR MEASURING THE PERMEABILITY OF A DRYING WIRE TO AIR

FIELD OF THE INVENTION

The invention relates to a method for measuring the permeability of a drying wire to air in which the measurement is carried out continuously while the drying wire moves.

The invention also relates to a device for measuring the permeability of a drying wire to air which is placed in the vicinity of a moving drying wire.

BACKGROUND OF THE INVENTION

Measurement of the penetrability to air of a drying wire, i.e., the permeability of drying wires, can be of significant concern, for example, in connection with monitoring the condition of the wires. These measurements of permeability should ideally be carried out in an industrial environment on the site of the machine through which the drying wire runs. Permeability meters are included, for example, in the standard equipment of every paper mill, and they are used, in particular, for measurements of the permeability of plastic wires.

It is a known phenomenon that drying wires tend to be blocked by dust or as a result of a phenomenon called mangling when the wire mesh size becomes smaller, which blockage lowers the permeability of the wire. A certain permeability is, however, highly important for the operation of a drying wire, for example, in view of the operation and runability of pocket ventilation devices which operate in the same machines as the drying wires. Based on measurements of permeability, it is usually decided whether a wire in a paper machine must be replaced or cleaned.

Measurement of the permeability of a drying wire can also be used in order to monitor and/or control the operation of devices for cleaning or washing drying wires. From such measurements of permeability, it is possible to ascertain the condition of the wire at each particular time, in which case, when necessary, the wire can be replaced before it is broken.

Furthermore, measurement of the permeability of a drying wire is also used by drying wire manufacturers, who typically measure the permeability in connection with the quality control of the manufacturing process in order to establish the uniformity of the quality of the drying wire.

In the measurement of the permeability of drying wires, it is a drawback of some prior art methods and devices that the paper machine must be stopped for the time of the permeability measurement of the drying wire. For this reason, the measurement has resulted in highly remarkable costs, for standstill time of a paper machine is very expensive.

In the prior art, Finnish Patent Application No. 872764 describes a method and device for the continuous measurement of the porosity of a web, wherein the vacuum produced by a suction blower is measured continuously by means of a measurement detector having a measurement head and the vacuum is maintained as constant as possible by means of a regulator which controls the suction blower. From the measured quantity of flowing air and from the other parameters of the air and the web received from the measurement detectors, the porosity of the web gliding over the measurement head is calculated. However, it is a drawback in this prior art construction that it is not possible to determine small flow quantities with a large degree of accuracy. It is a further problem that measurement arrangements with contact between the drying wire and a surface of the measurement device, e.g., a measurement head, which include or constitute rubbing faces, are not suitable for use in connection with drying wires.

In addition, Finnish Patent No. 93,397 describes a method and measurement device for measurement of the permeability to air of a felt in a paper machine in which the flow of air produced by a suction box through the felt is passed through a measurement pipe that forms the measurement duct, and the air flow in the measurement duct is measured by means of a pitot tube arranged therein. In the measurement device, there is a suction nozzle placed against the felt at the side opposite to the suction box. A suction pipe that forms the measurement duct is connected to the suction nozzle. The pitot tube is arranged in the suction pipe and a meter is connected to the pitot tube by means of a connector part and ducts in order to measure the pressures produced by the flow of air in the suction pipe. However, as is the case with the prior art construction described above, in this prior art measurement method and device, it is a problem that the method is not suitable for accurate measurement of small flow quantities nor for measurement of drying wires, because in the arrangement, there is contact between the drying wire and a part of the arrangement, in which case, rubbing faces are involved resulting in certain disadvantages.

Furthermore, Finnish Patent No. 77,119 describes a method for measuring the penetrability to air, i.e., the permeability, of fabrics permeable to air in a paper machine, in particular of a wire or felt. In the method, the fabric permeable to air, such as a wire, is passed over at least one roll, in which case, when the fabric runs, a pressure is formed at the inlet side of the fabric in the inlet nip between the moving fabric and the roll face, and a vacuum is formed at the outlet side of the moving fabric in the outlet nip of the fabric between the fabric and the roll face. The pressure and vacuum depend on the permeability of the fabric permeable to air. According to this method, at least one device is installed below the permeable fabric, such as a wire, which is sealed in relation to the face of the moving roll so that an at least partly closed pressure space is formed between the device, the roll face and the fabric, which may be a wire. When the fabric permeable to air moves, then the pressure is measured from the pressure space, and from the measured value of pressure, the permeability of the fabric permeable to air is calculated. In this construction, problems may arise in view of the fact that the pressure values of the pumpings of air produced by the wire face are very low and often do not depend on the wire permeability.

OBJECTS AND SUMMARY OF THE INVENTION

It is an object of the present invention to provide a method and device for measuring the permeability of a drying wire to air, in which the drawbacks of the prior art constructions are substantially eliminated or at least minimized.

It is a particular object of the present invention to provide a new and improved method and device for measuring the permeability of a drying wire to air which are easier to operate and quicker than the prior art methods and devices for similar measurement and which are also well suitable for measurement of the permeabilities of wires in their site of operation without stopping the paper machine and suitable for use in the measurement of permeability Carded out by wire manufacturers.

It is another object of the invention to provide a new and improved method and device for measuring the permeability of a drying wire to air which is efficient and can be used by drying wire manufacturers as well as in operating paper machines.

In view of achieving the objects stated above and others, in the method in accordance with the present invention, the drying wire is guided to run so that it passes over and in the vicinity of a blow box and a measurement box free of contact whereby the pressure in the measurement box and/or the relative change in this pressure is/are measured when the blow box is operating whereby a pressure differential is generated between the blow box and the measurement box such that the pressure in the measurement box is relative to the permeability of the drying wire. The measured pressure and/or the relative change in the pressure is/are compared with earlier measurement results and/or starting values (i.e., reference values), the permeability of the drying wire to air is determined on the basis of comparison of the pressure and/or of the relative change in the pressure. The contact-free measurement is produced by guiding the flow into or out of the measurement box to pass through the gap between the measurement box and the moving drying wire.

The device in accordance with the present invention comprises a blow box and a measurement box, the drying wire being arranged to pass over and in the vicinity of these boxes free of contact so that the flow into or out of the measurement box is guided to pass through the gap between the measurement box and the drying wire. The device also includes a pressure gauge for measuring the pressure in the measurement box and/or the relative change in the pressure in the measurement box. The measurement box is arranged relative to the blow box such that a pressure differential is generated between the blow box and the measurement box whereby the pressure in the measurement box is relative to the permeability of the drying wire.

By means of the present invention a number of significant advantages are obtained over the prior art constructions. Of these advantages, e.g., the following should be mentioned. By means of the method and the device in accordance with the invention, measurement of the permeability of drying wires can be performed at their operating site without stopping the paper machine or the machine in which the permeability of the drying wires is to be measured. The measurement of permeability can be carried out continuously, i.e., the condition of the wire can be monitored constantly. The measurement can be carried out as a block measurement so that the measurement results are obtained from several different points in the direction of width of the wire. The device can also be arranged in a mobile equipment fixed in the vicinity of the wire face in which case it is possible to measure a continuous permeability profile in the cross direction of the wire. Based on the measurement results obtained, it is possible to clean a blocked drying wire or to replace a wire that is in bad condition before the wire actually breaks, in which case the replacement of the wire alone makes stopping of the paper machine necessary.

It is an important feature of the invention that the flow-through required by the measurement box, i.e., the flow of a medium such as air into or from the measurement box relative to the pressure differential generated between the blow box and the measurement box and the permeability of the drying wire, is guided to take place between the measurement box and the moving face, whereby, at the same time, a contact-free measurement arrangement is obtained.

In accordance with the invention, at one side of the drying wire, there is a blow box that generates a pressure (also referred to as a positive pressure herein) or a vacuum (also referred to as a negative pressure herein) and operates, for example, with the "UNO-RUN-BLOW-BOX"™ nozzle principle, which blow box is placed apart from the wire face. By means of the blow box, a zone of pressure or vacuum is produced between the box and the drying wire. The measurement box is also placed apart from the wire face. The blowing from the blow box to create the pressure or vacuum results in a pressure differential being formed between this pressure or vacuum and the pressure in the measurement box. In the measurement process, the pressure in the measurement box and/or the relative change in this pressure is/are measured when the blow box is switched on to blowing, whereby the permeability of the wire and/or the change in permeability is/are established in comparison with earlier measurements/starting values (reference values), and in this manner, the need to clean/replace the wire can be determined.

When the arrangement in accordance with the invention is used for permeability measurements carried out in connection with the manufacture of the wire, the measurement takes place typically at a low speed or a crawling speed, for example about 10 meters per minute. In this case, it is possible to use support rolls by whose means the drying wire is kept at the correct distance from the blow box and from the measurement box, the drying wire thus passing by both the blow box and the measurement box free of contact. The disadvantages of a contact measurement technique are therefore avoided. It is pointed out that it is also possible to use support rolls in connection with a measurement of the permeability of the drying wire in a paper machine or other machine in which the drying wire operates.

In accordance with the invention, in a paper machine, the measurement is carried out preferably at the operating speed or running speed of the machine. It is also possible to carry out the measurement at a crawling speed, in which case it is possible to record the permeability profile of the wire in the longitudinal direction. At full running speed, the average level of permeability of the wire may be measured, which level can be compared, for example, with the level of permeability of a new wire, whereby the need of cleaning is demonstrated.

The device in accordance with the invention can be mounted as fixed at its measurement site, or it can be constructed as mobile, for example, on a profile beam. According to the invention, devices can be placed, in the direction of width of the wire, for example, at both edges of the wire and in the middle area of the wire, or it is possible to construct an arrangement in which a number of boxes are used and spaced in the transverse direction of the wire, whereby the whole width of the wire can be covered to thereby obtain a continuous permeability profile of the drying wire in the transverse or cross-direction of the drying wire.

The method and device of measurement in accordance with the invention can be applied to measurement of the permeability of drying wires in single-wire draw and so also to measurement of the permeability of drying wires in twin-wire draw.

In the following, the invention will be described in detail with reference to the figures in the accompanying drawing. The invention is however, in no way strictly confined to the details shown in the figures.

BRIEF DESCRIPTION OF THE DRAWINGS

The following drawings are illustrative of embodiments of the invention and are not meant to limit the scope of the invention as encompassed by the claims.

FIG. 6 is a schematic illustration of an exemplifying embodiment in which measurement devices are placed in the direction of width of the drying wire at the edges of the drying wire and in a middle area of the drying wire in accordance with the invention.

FIG. 7 is a schematic illustration of an arrangement in which the permeability of the drying wire is measured in the cross direction of the machine across the entire width by using separate blocks in the blow box in accordance with the invention.

FIG. 8 is a schematic illustration of a measurement device intended for a low speed, in particular for use in connection with the manufacture of wires in accordance with the invention.

DETAILED DESCRIPTION OF THE PREFERRED EMBODIMENTS

Figure 1:
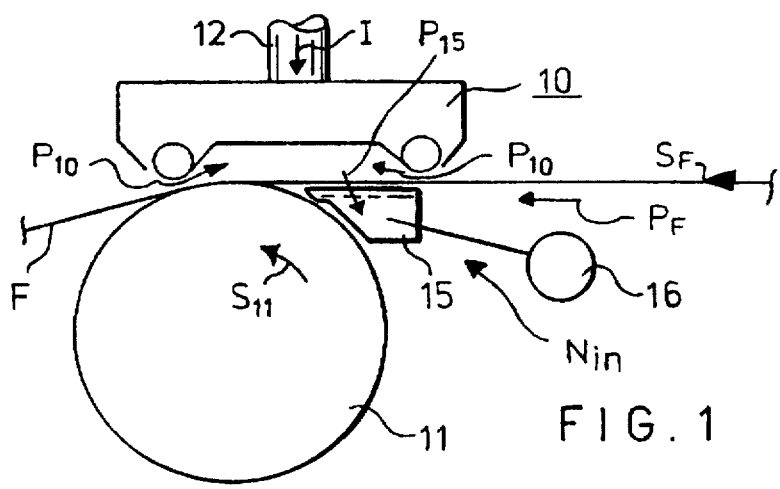
FIG. 1 is a schematic illustration of the measurement of permeability of a drying wire in an inlet nip of the drying wire in accordance with the invention.

In the exemplifying embodiment of the invention shown in FIG. 1, the penetrability to air of a drying wire, i.e., the permeability of a drying wire F, is measured in an inlet nip $N_{in}$ of the drying wire F with respect to a wire guide roll 11. The running direction of the drying wire F is denoted by the arrow $S_F$, and the wire guide roll 11 revolves in the direction indicated by the arrow $S_{11}$. A blow box 10 that generates a pressure is placed at the side of the drying wire F opposite to the wire guide roll 11. An air flow I is passed out of a feed pipe 12 into the box 10. Out of the blow box 10, the air is passed as edge-nozzle blowings $P_{10}$ onto the face of the wire F so that the blowings $P_{10}$ are directed from the nozzles toward the middle of the blow box 10. As such, the area between the wire F and the box 10 is subjected to a pressure and air is passed from this area in the middle of the blow box 10 through the drying wire F into a passive measurement box 15 if the drying wire F has any remaining permeability. The quantity of air being passed to the measurement box 15 from the area of positive pressure generated by the blow box 10 depends on the permeability of the drying wire F. The pressure in the measurement box 15 is measured by means of a pressure gauge 16 or other suitable air pressure measuring means. Based on the pressure measurement, the relative pressure and/or the change in pressure is/are obtained. On the basis of the relative pressure and/or the change in pressure, the permeability and/or the relative permeability value is/are determined. The pressure gauge 16 is read, for example, in a situation in which the blower does not blow air into the box 10 and in a situation in which the blower blows air into the box 10. In this manner, a relative pressure value or values is/are obtained (and constitute reference values of sort), which can be compared, for example, with the pressure value measured in connection with the introduction of the wire to operation, and thereby the permeability to air of the drying wire F can be determined during operation and movement of the drying wire.

Along with the drying wire F, air is pumped into the inlet nip $N_{in}$, as the air flow $P_F$, a certain positive pressure being formed in the inlet nip $N_{in}$. Out of the blow box 10, air flows $P_{10}$ are blown into the gap between the drying wire F and the box 10, whereby the top side of the wire F is pressurized. Then the air passes as the air flow $P_{15}$, through the wire F and enters into the measurement box 15 and produces a change in the pressure in the measurement box 15. The pressure in the measurement box 15 is read from the pressure gauge 16, whereby a pressure value is obtained, on whose basis a permeability value is determined, which is compared with the permeability value of the wire F, for example with a measurement result obtained in connection with the introduction of the wire or with an earlier measurement result (reference values). When the wire F is partially blocked, the measurement value of the measurement box 15 becomes lower, and when the wire F is fully blocked, the air flow $P_{15}$ cannot pass through the wire and does, thus, no longer produces an increase in the pressure in the measurement box 15. From this absence of change (lack of a pressure increase) in the measured pressure, it can be realized that the wire must be cleaned or replaced.

Figure 2:
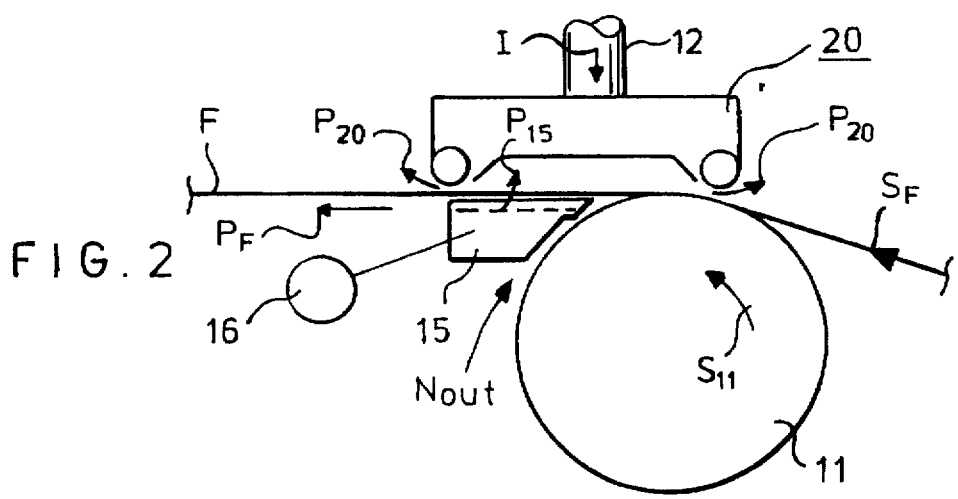
FIG. 2 is a schematic illustration of the measurement of the permeability of a drying wire in an outlet nip of the drying wire in accordance with the invention.

In the exemplifying embodiment shown in FIG. 2, the permeability measurement is arranged to take place in the outlet nip $N_{out}$ of the drying wire F at the wire guide roll 11. A blow box 20 that generates a vacuum is placed at the outlet side of the nip at the side of the drying wire F opposite to the wire guide roll 11. Air is passed out of the feed pipe 12 into the blow box 20. Out of the blow box 20, the air is passed as edge blowings $P_{20}$ away from the blow box 20, whereby an area with a vacuum is formed between the drying wire F and the blow box 20 by the effect of the ejection effect of the air flows $P_{20}$ which eject air from the middle area of the blow box 20. An air flow is thus caused to depart from the passive measurement box 15 by the effect of the upper vacuum denoted by the arrow $P_{15}$ which is perforce passed through the drying wire F. The pressure gauge arranged in association with the passive measurement box 15 is denoted by the reference numeral 16 although other pressure measurement means are of course usable in the invention without deviating from the scope and spirit thereof. The running direction of the drying wire F is denoted by the arrow $S_F$, and the wire guide roll 11 revolves in the direction indicated by the arrow $S_{11}$.

The drying wire F takes away air along with it, by virtue of its movement, and this air flow is denoted by $P_F$, whereby the outlet nip $N_{out}$ is subjected to a vacuum. At the side of the wire F opposite to the outlet nip $N_{out}$ there is the blow box 20 that generates a vacuum, the air flows $P_{20}$ being produced by means of edge blowings at the box, which air flows $P_{20}$ produce a vacuum between the wire F and the blow box 20. Then, air also flows from the opposite measurement box 15 through the wire F as the flow $P_{15}$ to the side of the blow box 20 and produces an increased vacuum in the measurement box 15. When the pressure value of the measurement box 15 is measured by means of the pressure gauge 16, a pressure value is obtained, which can be compared with the measurement result obtained in connection with the introduction of the wire or with a result obtained when the blow box 20 is not in operation. Then, a relative or reference pressure value is obtained, on whose basis the permeability value is determined. When the wire F is fully blocked as a result of contaminants or other obstructions, no more air flows from the side of the measurement box 15 to the side of the blow box 20, at which stage the vacuum in the measurement box 15 is minimal, i.e., the situation corresponds to the reading value with which there is no effect of the blow box 20.

The width of the blow box 10, 20 is, for example, from about 0.2 meter to about 1 meter, and in it, for example, nozzle pressures of from about 300 Pa to about 5000 Pa can be used, and the pressure level of the blow box is from about 50 Pa to about 500 Pa, and the pressure in the measurement box is from about 20 Pa to about 400 Pa.

In the embodiments shown in FIGS. 1 and 2, the change in the permeability of the drying wire F is measured while the machine is in operation. The measurements of the drying wire are carried out at suitable time intervals, for example as automatically programmed once a week, or the system can be connected with a monitoring equipment, which gives an alarm when the degree of blocking of the wire approaches a limit indicative of the necessity for cleaning of the drying wire.

Figure 3:
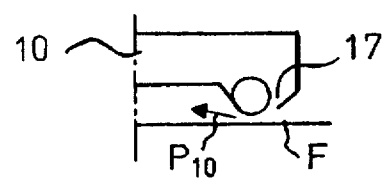
FIG. 3 is a schematic illustration of an edge nozzle of a blow box that generates a pressure as shown in FIG. 1 and is used in the method and device in accordance with the invention.

FIG. 3 is a schematic illustration of an edge nozzle 17 of a blow box 10 as shown in FIG. 1, out of which nozzle the air flow $P_{10}$ is blown onto the drying wire F. By means of the shape of the nozzle 17, i.e., by appropriate construction thereof, turning of the air flow $P_{10}$ is obtained in a direction toward the area between the blow box 10 and the wire F so as to produce positive pressure in the area between the edge nozzles 17 (FIG. 1).

Figure 4:
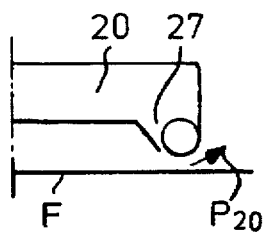
FIG. 4 is a schematic illustration of an edge nozzle of a blow box that generates a vacuum as shown in FIG. 2 and is used in the method and device in accordance with the invention.

FIG. 4 is a schematic illustration of an edge nozzle 27 of a blow box 20 that generates a vacuum as shown in FIG. 2 out of which nozzle the air flow $P_{20}$ is blown onto the drying wire F. By means of the shape of the nozzle 27, i.e., the construction thereof, the air flow $P_{20}$ is turned away from the area between the blow box 20 and the drying wire F whereby a vacuum is produced by means of the ejection effect of the air flows $P_{20}$ in the area between the edge nozzles 27 (FIG. 2).

The blow box 10,20 is mounted in the vicinity of the wire guide roll 11, whereby the deflection of the wire has been minimized and at the same time the sealing of the measurement box 15 can be arranged more easily.

Figure 5:
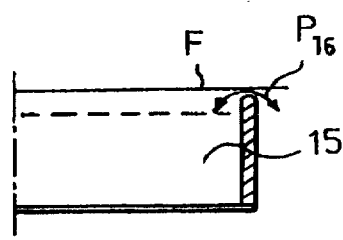
FIG. 5 is a schematic illustration of the roll face of the measurement box used in the method and device in accordance with the invention and of the lateral seals and end seals connected with the measurement box.

FIG. 5 shows the roll and wire face of the measurement box 15 and the related edge and end seals. The seal faces of the measurement box 15 do not contact the wire F, but they permit a certain leakage flow $P_{16}$ into or out of the measurement box 15 through a gap or space thus defined between the measurement box 15 and the drying wire F. As the distance of the seal from the wire face remains substantially constant, the pressure formed in the measurement box or the change in this pressure depends on the flow taking place through the wire. Since the flow-through $P_{16}$ required by the measurement box is controlled to take place expressly between the box and the moving face, at the same time a measurement arrangement free from contact is obtained.

As shown in FIG. 6, in this exemplifying embodiment of the invention, a plurality of blow boxes 10,20 are placed in the direction of width of the drying wire F, specifically one in each lateral area of the drying wire F and one in a middle area of the drying wire F (relative to a direction transverse to the running direction of the wire). By means of this arrangement, it is possible to compare the permeability of the wire at different points along the width of the drying wire F. This comparison can be useful for determining present and future use of the drying wire.

As shown in FIG. 7, the blow box 10,20 can also be a continuous box extending across substantially the entire width of the drying wire F in the cross direction of the machine or it may be formed as a plurality of adjoining but separate blocks 18,28. In these situations, it is possible to measure the permeability of the drying wire at a number of points in the cross direction of the machine, corresponding to the location of each block.

FIG. 8 shows a measurement device intended for a drying wire moving at a low speed, (e.g., a crawling speed) in particular to be used by manufacturers of drying wires. In this device, the blow box 10 is placed above the drying wire F and is fixed to the measurement location by means of support constructions 35. The measurement box 15 is arranged below the drying wire F and is supported on the frame constructions 32,33 and 34, and the wire F is kept at a substantially constant distance from the measurement box 15, for example, by means of support rolls or glide faces or equivalent 31 (the measurement box 15 and opposed blow box 10 being positioned between the two support rolls 31). The frame constructions 34,35 can be mounted either as fixed or as displaceable, in which case it is possible to carry out the measurements at a certain location in the direction of width of the wire F, or to measure the cross-direction profile of permeability, respectively. The measurement diameter is, for example, from about 100 mm to about 500 min. The exemplifying embodiment shown in FIG. 8 is employed in particular for monitoring the manufacture of new wires F, in which case the wire runs preferably at a crawling speed, for example about 10 meters per minute. The measurement process is similar to the process described in relation to FIG. 1.

Figure 9:
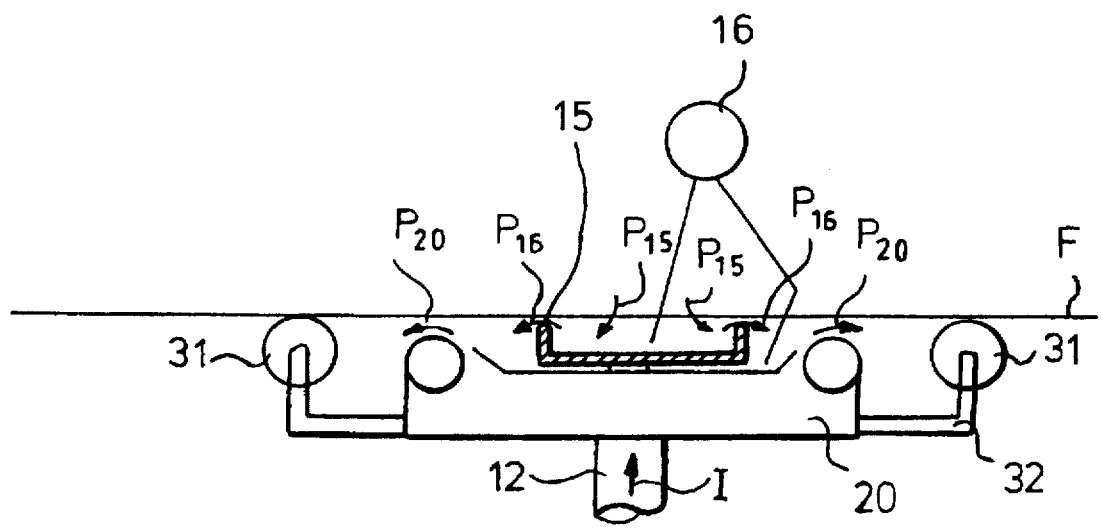
FIG. 9 is a schematic illustration of a measurement device intended for a low speed in which the blow box and the measurement box are placed at the same side of the drying wire in accordance with the invention.

FIG. 9 shows a measurement device intended for low speed permeability measurements, which is suitable in particular in connection with the manufacture of drying wires for measurement of their permeability to air. The exemplifying embodiment shown in FIG. 9 is substantially similar to that shown in FIG. 8, except that the measurement box 15 is placed at the same side of the wire F as the blow box 20. In the exemplifying embodiment shown in this illustration, the blow box 20 is a suction or vacuum box, but instead of a suction box it is also possible to use a pressure box. The measurement box 15 is placed inside the blow box 20, and out of the edge nozzles of the blow box 20, flows $P_{20}$ are blown, which produce a vacuum between the drying wire F and the blow box 20. Then the flows $P_{16}$ pass out of the measurement box 15 between the edges of the measurement box 15 and the drying wire F, whereby the vacuum formed in the measurement box 15 produces a flow $P_{15}$ through the drying wire F, in which connection it is possible to determine the permeability of the drying wire F by measuring the pressure in the measurement box 15 by means of the pressure gauge 16. Based on the measurement of pressure, the relative pressure and/or the change in pressure is obtained. Regarding its principle of measurement and the other constructions, the measurement device shown in this figure is substantially similar to that shown in FIG. 8, and corresponding parts are denoted with the same reference numerals.

Figure 10:
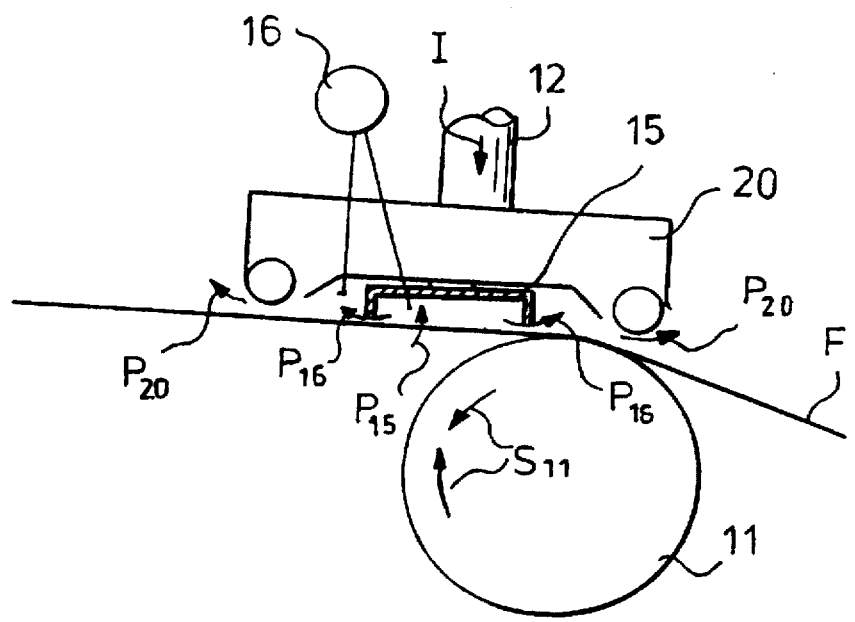
FIG. 10 is a schematic illustration of a measurement device to be used in a paper machine preferably at the running speed in accordance with the invention, in which device the blow box and the measurement box are placed at the same side of the drying wire.

In the exemplifying embodiment shown in FIG. 10, the measurement of the permeability of the drying wire F is carried out from a nip of the roll 11. The running direction of the wire F is free, and the relative pressure and/or the change in the pressure in the measurement box is/are measured by means of the pressure gauge 16. In the exemplifying embodiment shown in the figure, the blow box 20 is a suction or vacuum box. Out of the blow box 20, air flows $P_{20}$ are blown, which produce a vacuum in the area between the blow box 20 and the drying wire F, in which connection flows $P_{16}$ are passed out of the measurement box 15, which flows $P_{16}$ seal the gap between the drying wire F and the measurement box and produce a contact-free measurement process, and a flow $P_{15}$ is produced towards the measurement box 15 through the drying wire F. With respect to its basic principles, the measurement process is similar to that described above in relation to the embodiments in FIGS. 1-9.

The examples provided above are not meant to be exclusive. Many other variations of the present invention would be obvious to those skilled in the art, and are contemplated to be within the scope of the appended claims. For example, although several specific types of blow boxes for generating a pressure differential between the blow box and the measurement box are described, it should be understood that other means for generating such a pressure differential can be used in accordance with the invention without deviating from the scope and spirit thereof.

I claim:

1. A method for measuring the permeability of a drying wire to air during movement of the drying wire, comprising the steps of:

guiding the drying wire to pass over a blow box and a measurement box without the drying wire contacting the blow box or the measurement box, the measurement box being spaced from the drying wire such that air flows from or into the measurement box through a gap between the measurement box and the moving drying wire, generating a pressure differential between the blow box and the measurement box such that the pressure in the measurement box is relative to the permeability of the drying wire, measuring at least one of the pressure in the measurement box and a relative change in the pressure in the measurement box, comparing at least one of the measured pressure in the measurement box and relative change in the pressure in the measurement box to a previously measured or reference pressure values or a previously measured or reference relative pressure change value, and determining the permeability of the drying wire to air on the basis of the comparison of at least one of the pressure in the measurement box and the relative change in the pressure in the measurement box.

2. The method of claim 1, further comprising the steps of:

arranging the blow box and measurement box in a paper machine, and conducting the measuring step when the paper machine is running at a full running speed.

3. The method of claim 1, further comprising the steps of:

arranging the blow box and measurement box in a drying wire manufacturing machine, and conducting the measuring step when the drying wire manufacturing machine is running at a crawling speed.

4. The method of claim 1, wherein the step of generating the pressure differential between the blow box and the measurement box comprises the step of directing air from the blow box to produce a positive pressure in an area between the drying wire and the blow box, further comprising the step of:

arranging the measurement box on an opposite side of the drying wire from the blow box such that the air flow through the drying wire into the measurement box is a function of the permeability of the drying wire.

5. The method of claim 4, further comprising the steps of:

guiding the drying wire over a wire guide roll, and arranging the blow box and the measurement box in an area of an inlet nip of the drying wire and the wire guide roll, the inlet nip being subjected to a positive pressure by the effect of pumping by the drying wire.

6. The method of claim 1, wherein the step of generating the pressure differential between the blow box and the measurement box comprises the step of directing air from the blow box to produce a negative pressure in an area between the drying wire and the blow box, further comprising the step of:

arranging the measurement box on an opposite side of the drying wire from the blow box such that the air flow through the drying wire from the measurement box is a function of the permeability of the drying wire.

7. The method of claim 6, further comprising the steps of:

guiding the drying wire over a wire guide roll, and arranging the blow box and the measurement box in an area of an outlet nip of the drying wire and the wire guide roll, the inlet nip being subjected to a negative pressure by the effect of the evacuation of air produced by the drying wire.

8. The method of claim 1, wherein the step of generating the pressure differential between the blow box and the measurement box comprises the step of directing air from the blow box to produce a negative pressure in an area between the drying wire and the blow box, further comprising the step of:

arranging the measurement box on the same side of the drying wire as the blow box such that the air flow from the measurement box through the gap between the measurement box and the drying wire is a function of the permeability of the drying wire.

9. The method of claim 1, further comprising the steps:

passing the drying wire over a pair of support rolls or glide faces spaced from each other, arranging the blow box and measurement box between the support rolls or glide faces, and conducting the measuring step when the drying wire is running at a crawling speed.

10. The method of claim 1, wherein the measuring step comprises the step of measuring the permeability of the drying wire at a plurality of discrete locations in the cross direction of the drying wire.

11. The method of claim 1, wherein the measuring step comprises the step of measuring the permeability of the drying wire substantially across the entire width of the drying wire to obtain a continuous permeability profile in the cross-machine direction.

12. A device for measuring the permeability of a drying wire to air while the drying wire is moving, comprising a blow box arranged in the vicinity of and spaced from the drying wire such that the drying wire passes over said blow box without contacting said blow box, a measurement box spaced from the drying wire such that a gap is formed between said measurement box and the drying wire and the drying wire passes over said measurement box without contacting said measurement box, said blow box being arranged to generate a pressure differential between said blow box and said measurement box whereby the pressure in said measurement box is relative to the permeability of the drying wire, and measurement means for measuring at least one of the pressure in said measurement box and a relative change in the pressure in said measurement box, the permeability of the drying wire being determinable from said measured pressure in said measurement box and said measured relative change in the pressure in said measurement box.

13. The device of claim 12, wherein said blow box comprises nozzles arranged at edges of said blow box for producing edge blowings, said edge blowings causing a middle area of said blow box between said edges to be subjected to a positive pressure greater than the pressure in said measurement box.

14. The device of claim 12, wherein said blow box comprises nozzles arranged at edges of said blow box for producing edge blowings, said edge blowings causing a middle area of said blow box between said edges to be subjected to a negative pressure less than the pressure in said measurement box.

15. The device of claim 12, wherein the device is situated in a paper machine, the paper machine including a wire guide roll over which the drying wire runs, said blow box and said measurement box being arranged in an area of an inlet nip defined by said wire guide roll and the drying wire.

16. The device of claim 12, wherein the device is situated in a paper machine, the paper machine including a wire guide roll over which the drying wire runs, said blow box and said measurement box being arranged in an area of an outlet nip defined by said wire guide roll and the drying wire.

17. The device of claim 12, wherein said blow box comprises a plurality of blocks and said measurement box comprises a plurality of blocks, each of said blocks of said measurement box being aligned with a respective one of said blocks of said blow box, said measurement means being arranged to measure the pressure in each of said measurement boxes in order to obtain a permeability profile of the drying wire in the cross direction of the drying wire.

18. The device of claim 12, further comprising frame means for fixing said blow box and said measurement box in respective fixed positions, and guide means for guiding the drying wire over said blow box and said measurement box, said guide means being selected from the group consisting of a support roll and a glide face.

19. The device of claim 12, wherein said measurement means measure the pressure in said measurement box and a relative change in the pressure in said measurement box.

20. The device of claim 12, wherein said measurement means measure only a relative change in the pressure in said measurement box.

* * * * *